United States Patent [19]
Gergely et al.

[11] Patent Number: 6,096,343
[45] Date of Patent: Aug. 1, 2000

[54] INSTANT CALCIUM/SOYBEAN GRANULES, THEIR USE AND PROCESS FOR THEIR PREPARATION

[75] Inventors: Gerhard Gergely, Gartengasse 8, A-1053 Vienna; Irmgard Gergely, Vienna; Thomas Gergely, Vienna; Stefan Gergely, Vienna, all of Austria

[73] Assignee: Gerhard Gergely, Vienna, Australia

[21] Appl. No.: 09/179,391

[22] Filed: Oct. 27, 1998

Related U.S. Application Data

[60] Provisional application No. 60/063,674, Oct. 29, 1997.

[30] Foreign Application Priority Data

Oct. 29, 1997 [CH] Switzerland .............................. 2505/97

[51] Int. Cl.[7] .............................. A61K 9/16; A01N 65/00
[52] U.S. Cl. ......................................... 424/499; 424/195.1
[58] Field of Search ................................. 424/195.1, 499; 514/456

[56] References Cited

U.S. PATENT DOCUMENTS

| | | | |
|---|---|---|---|
| 5,424,331 | 6/1995 | Shlyankevich | 514/456 |
| 5,487,894 | 1/1996 | Kovacs | 424/195.1 |
| 5,599,556 | 2/1997 | Meyer et al. | 424/491 |
| 5,654,011 | 8/1997 | Jackson et al. | 424/635 |

OTHER PUBLICATIONS

Remington: The Science and Practice of Pharmacy. Mack Publishing Co. 19th ed. pp. 1623–1625, 1995.

XP–002069253. Derwent Abstracts. 1996. Tong, K. et al. Bone Mash calcium–supplementary Paste. CN1128108.

*Primary Examiner*—Thurman K. Page
*Assistant Examiner*—Alysia Berman
*Attorney, Agent, or Firm*—Oliff & Berridge, PLC

[57] ABSTRACT

The invention relates to instant granules which contain at least one isoflavone-containing soybean material, at least one calcium compound and optionally vitamin D3 or other additives in granules in which the particles of soybean material and the calcium compound are present intimately mixed and bound to one another preferably with the aid of a binder—optionally with the addition of a surfactant.

The invention furthermore relates to a process for the preparation of the instant granules and to their use.

17 Claims, No Drawings

INSTANT CALCIUM/SOYBEAN GRANULES, THEIR USE AND PROCESS FOR THEIR PREPARATION

This nonprovisional application claims the benefit of U.S. Provisional Application No. 60/063,674, filed Oct. 29, 1997.

The invention relates to instant granules according to the preamble of claim 1, a process for their preparation, and the use of a mixture of at least one soybean material with at least one pharmaceutically permissible calcium compound.

EP-A2 398 867 describes a cocoa-containing drink for children and young persons in the growth phase which has a high nutritional value and, in addition to cocoa, also contains sweeteners, flavors, wheatgerms, soybean protein, calcium and magnesium, the vitamins B1, B2, B6 and C and lecithin as emulsifier. Lactose may be added to promote calcium absorption but is physiologically undesirable, particularly in the proposed amounts.

On the other hand, instant granules according to the defining features of claim 1, which, owing to their high dose of calcium ions and of the essential ingredients of soybean, namely the isoflavones, could not to date be brought into a form capable of oral administration, are proposed according to the invention. Furthermore, the use of vitamin D3 or of sodium monofluorophosphate (in contrast to the EP-A1 mentioned at the outset and to conventional calcium-containing tablets) for improving the calcium absorption, and the use of such granules for the treatment and prevention of osteoporosis, are proposed according to the invention.

Suitable isoflavone donors are in particular concentrated soybean isoflavones from CentralSoya® (U.S.A) containing 5% of isoflavones or those from NovaSoy® (U.S.A) containing 40% of isoflavones.

Soybean products have for some time been known as effective components in the prevention of osteoporosis (Journal of Nutrition, March 1995). Various studies have backed up this assumption; the eating habits in Asiatic countries compared with those of Western countries have shown a relationship to the occurrence of osteoporosis.

In Western countries, osteoporosis is treated by various measures, in particular with high doses of calcium in combination with vitamin D3. There is now a large number of scientific publications in which, owing to their content of phytoestrogens, soybean protein powders play an important role in the prevention of menopausal symptoms and osteoporosis (Annual Review of Nutrition 1997). Owing to their estrogen activity, they can to a certain degree prevent osteoporosis. A report of the Royal Hospital for Women in Australia reveals that, owing to their high phytoestrogen content, soybean products have an advantageous effect in the treatment of osteoporosis. A further study states that soybean proteins can be effectively used for preventing atrophy of the bone due to hormone deficiency.

Regarding the prior art: It is known (publication "Bone mash calcium supplementing paste") that calcium and a soybean material can be administered in a paste. This is a pasty material which contains predominantly powdered pig and cattle bones and contains only 2–3% of soybean powder, but no indication of a solution to the problem of instant granules containing calcium and soybean [sic].

The object of the invention was to develop a product to bring the desired soybean material in powder form together with calcium compounds and optionally vitamins, in particular vitamin D3, fluorine compounds and/or amino acids into the pharmaceutical form of instant granules which contain a considerable amount of soybean material together with organic and/or inorganic calcium-containing substances and, on dissolution, can be suspended in a glass of water.

In the preparation of instant granules, the problem of granulation of the soybean material and the achievement of good wettability of the granules had to be solved. Another problem was to suspend both the calcium compounds and the soybean material so that it was possible to obtain a suspension which was stable—for at least 5 minutes—without sedimentation.

According to the invention, it is now possible to produce instant calcium/soybean granules for the preparation of both pH-neutral drinks and acid-containing drinks, the common feature of which granules is that the poorly wettable soybean powders are granulated with surfactant substances together with calcium compounds to give a readily suspendable drink in which both the consumption of soybean material and the consumption of the calcium compound are associated with one another in a pleasant and expedient manner.

The object was for a dose to contain about 500 to 1200 mg of calcium ions and also 0.1 to 10 g of soybean material, and in addition to this vitamin D3, preferably in an amount of 100 to 1000, in particular 200 to 800, IU, or fluorine compounds, for example in an amount of 50 to 100 mg of sodium monofluorophosphate, may be incorporated for the prevention or therapy of osteoporosis.

Suitable soybean materials are both defatted and fat-containing soybean flours, defatted soybean flours being preferred, and furthermore soybean protein powder, pulverized soybean meal (full-fat or defatted) or mixtures of these products.

However, soybean material which is rich in the two most important isoflavones, genistein and daidzein, is preferred. Based on the consumption of soybean products in Japan, a typical daily dose of isoflavones is about 50 mg per person (according to American Journal of Chemical Nutrition 1995). In the case of soybean material which is rich in isoflavones and contains, for example, 40% of isoflavones, only a dose of, for example, about 125 mg of soybean material is required, i.e. there is no longer any need to administer large amounts of soybean flour. Furthermore, soybean isoflavone concentrates which contain all essential isoflavones, such as daidzeins, glyciteins and genisteins, are also commercially available. It is also possible to use commercial concentrated soybean proteins or soybean protein concentrates which contain the essential isoflavones—preferably in enriched form.

Suitable calcium carriers are mainly organic calcium compounds, such as, for example, calcium glycerophosphate, tricalcium dicitrate, monocalcium citrate, calcium levulinate, calcium malate and others.

Suitable inorganic calcium compounds are mainly calcium carbonate, calcium biphosphate, calcium chloride, calcium phosphate and others.

The choice of calcium compounds makes it possible to prepare a large number of drinks from acidic to neutral with a very wide range of flavours from fruity to creamy. Of course, the resulting granules may also be sweetened in a variety of ways with the permitted sweeteners, such as sodium cyclamate, saccharin Na, aspartame or acesulfame, and may be provided with flavors.

Furthermore, fillers for the formation of granules are used, such as maltodextrin (e.g. Maltrin M 700®, and/or sugar alcohols, such as sorbitol or mannitol; glucose, fructose, lactose, sucrose, corn starch and/or hydrolyzed starches may also be used.

As additives to the combination of soybean with calcium, it is also possible to integrate vitamins, for example the vitamins of the B complex, fat-soluble vitamins, such as A, D and E, and folic acid, biotin, cyanocobalamin, nicotinamide, calcium pantothenate and/or vitamin C, as well as trace elements, such as, for example, manganese, copper and zinc, and also minerals, such as potassium, magnesium, iron, etc. In addition, enrichment with lysine, myoinositol and further amino acids, for example arginine aspartate, valine, isoleucine, alanine, cystine, glutamic acid, glycine, phenylalanine, hystidine, threonine, tyrosine, etc., is also possible.

The preparation of instant calcium/soybean granules having relatively high calcium doses is illustrated with reference to some examples, and an instant calcium/soybean product which also contains vitamins, minerals and trace elements and some amino acids in addition to calcium is also described.

The preparation is best carried out by moistening and granulating the calcium compound together with the fillers and the optionally added minerals and/or sweeteners with the solution of a binder and then applying the soybean powder to the moist granules and warming the material to 60° C. while stirring, the initial granulation of the soybean material taking place as a result of the moisture present. The binder solution contains, as a solvent, alcohol or a mixture of alcohol and water and, as an additive, a surfactant. The resulting product is then dried, vacuum drying being preferred; however, it is also possible to dry the granules in a fluidized-bed dryer. Drying gives free-flowing granules in whose grains the particles of the calcium compound(s) and of the pulverulent soybean material are present as an intimate mixture. To achieve a uniform particle size if required, the granules can be sieved, for example to a particle size of 1.5 to 2.5 mm, and packed in individual cans.

The binders which are required to granulate the two substances, i.e. the soybean flour and the calcium compound, should preferably be substances which are soluble in organic solvents or solvent mixtures with water. These include primarily polyvinylpyrrolidone, polyethylene glycol 6000 and also concentrated solutions of sugar alcohols. However, sucrose, fructose and glucose may also be used. As mentioned at the outset, alcohol-soluble substances or substances soluble in organic aqueous solvents are preferred because, on the one hand, granulation with purely aqueous binder solutions may adversely affect in particular the soybean protein powder with its active principles and because, on the other hand, drying of calcium/soybean granules treated with aqueous solution is possible only with difficulty.

Advantageously used surfactants which may be employed for better wettability of the various soybean powders or for improvement of the suspendability of calcium/soybean granules are sodium dioctylsulfosuccinate, polysorbates, polyoxyethylene glyceryl fatty acid esters, sodium laurylsulfate and the like.

The invention is to be illustrated with reference to some examples:

EXAMPLE 1

Preparation of calcium/soybean granules containing 500 mg of calcium and 400 IU of vitamin D3:

125 parts by weight of calcium carbonate, 25 parts by weight of sorbitol, 37 parts by weight of sucrose, 400 parts by weight of maltodextrin and 4 parts by weight of aspartame are uniformly mixed with heating and stirring. The mixture is wet with a solution consisting of 1.5 parts by weight of polysorbate, 16.8 parts by weight of liquid glucose syrup (equivalent to 13.5, based on solid) in 50 parts by weight of 40% ethanol and uniformly distributed for 3 minutes. 770 parts by weight of soybean flour are added and the mixture is heated to 60–65° C. while stirring, granulation taking place. The product is then dried, both vacuum drying and belt drying being possible.

400 IU of vitamin D3 and flavors are added to the granules sieved to 1.5–2.0 mm. In addition to 500 mg of calcium ion and 400 IU of vitamin D3, a dose of 14 g furthermore contains 7.7 g of soybean flour, corresponding to a content of 15.4–23 mg of isoflavones (according to Technical Bulletin, 1 gram of soybean flour contains 2–3 mg of isoflavones). When introduced into water and stirred briefly, this gives a milky, pleasant-tasting suspension.

As mentioned in Example 1, instead of soybean flour it is also possible to process soybean proteins and soybean material enriched with isoflavones, the required amount of granulating solution being dependent to a certain degree on the soybean material used.

In the case of organic calcium salts, the calcium salts may also be mixed with soybean flour and then granulated with an alcoholic or alcoholic-aqueous solution containing a binder.

EXAMPLE 2

As an example of an acidic drink:

6 parts by weight of pulverulent soybean material are mixed with 5.75 parts by weight of monocalcium citrate, heated to 50° C. and granulated with a solution consisting of 0.02 part by weight of polyvinylpyrrolidone in 0.2 part by weight of ethanol. A dose of 11.8 g contains 1000 mg of calcium ions and 6 g of soybean product, corresponding to a content of 12–18 mg of isoflavones (or corresponding to a content of 25–40 mg of isoflavones when an enriched soybean material is used), and can be provided with fruit flavors, sweeteners and colors.

EXAMPLE 3

With calcium glycerophosphate as the calcium compound:

The preparation is carried out analogously to the preceding Examples. 10 parts by weight of pulverulent soybean material are mixed with 5.2 parts by weight of calcium glycerophosphate (corresponding to 1000 mg of calcium ion) in a granulator. The product is heated to 50° C. with mixing and is granulated with a solution consisting of 0.7 part by weight of ethanol, 1 part by weight of polyethylene glycol 6000, which is melted, and 0.004 part by weight of sorbitan oleate (Tween®). The product is dried with stirring, sieved through a sieve of 1 to 2 mm, preferably by means of a vacuum, and mixed with 0.7 part by weight of flavor and, if desired, with a corresponding amount of sweetener and optionally of color.

A dose of 16.2 g—corresponding to 1000 mg of calcium and 20–30 mg of isoflavones—gives a readily suspendable drink.

EXAMPLE 4

Preparation of calcium/soybean granules containing 160 mg of calcium and minerals (magnesium and iron), trace elements, vitamins and amino acids:

The following are introduced into a vacuum granulator: 688 parts by weight of calcium hydrogen phosphate, 44 parts by weight of potassium carbonate, 286 parts by weight of trimagnesium dicitrate, 21 parts by weight of iron gluconate, 625 parts by weight of lysine HCl, 12.5 parts by weight of myoinositol, 4000 parts by weight of maltodextrin, 60 parts by weight of aspartame, 200 parts by weight of citric acid and 363 parts by weight of sucrose are homogeneously mixed. A solution consisting of 15 parts by weight of polysorbate and 135 parts by weight of liquid glucose syrup dissolved in 490 parts by weight of 40% ethanol is applied to this mixture and uniformly distributed. 8300 parts by weight of soybean flour are added to this moistened mixture and the latter is heated to 60° C. with stirring, granulation taking place. The moist granules are dried at a temperature of 40–55° C. by means of a vacuum while stirring. A mixture of vitamins of the B complex, vitamin C and vitamin A, D and E, and furthermore trace elements, such as manganese, copper and zinc, and optionally further amino acids may be mixed with the granules which have been dried and sieved to the desired particle size. With orange and lemon flavors, a dose of 14–18 g (containing 8.3 g of soybean flour or 16.6–25 mg of isoflavones), the product gives a readily suspendable, pleasant-tasting drink.

To achieve optimum dissolution of the instant granules, according to the invention the soybean material (e.g. soybean flour) is preferably granulated either with a soluble organic calcium compound or with a mixture of a suitable filler and an insoluble inorganic calcium compound with the aid of a suitable binder, such as, for example, glucose syrup, which contains a wetting agent, such as, for example, polysorbate. In this way, it is ensured that the protein-containing soybean material (e.g. soybean flour) is thoroughly wet and does not form lumps and therefore also does not have is disadvantage that it is difficult to suspend in a drink. The filler or the soluble calcium compounds are in fact superficially dissolved, the soybean product is incorporated there and the instant granules can then be much more readily suspended. The addition of a polysorbate to a glucose syrup as granulating solution has proven very expedient.

What is claimed is:

1. A process for the preparation of instant granules that comprise at least one isoflavone-containing soybean material and at least one pharmaceutically permissible calcium compound, wherein the granules contain, per dose, 0.1 to 10 g of a soybean material containing 5 to 100 mg of isoflavones, 100 to 1200 mg of calcium ions and a binder, and wherein at least one pulverulent calcium compound is wetted with an organic or aqueous organic solution of a binder, after which at least one pulverulent, isoflavone-containing soybean material is applied, with stirring and heating, whereafter the resulting granules are dried and packed in single doses.

2. A process for the preparation of instant granules that comprise at least one isoflavone-containing soybean material and at least one pharmaceutically permissible calcium compound, wherein the granules contain, per dose, 0.1 to 10 g of a soybean material containing 5 to 100 mg of isoflavones and in addition 100 to 1200 mg of calcium ions and a binder, and wherein at least one organic calcium compound is initially taken together with at least one pulverulent, isoflavone-containing soybean material and optionally further additives, mixing is carried out, wetting is then effected with an organic or aqueous organic solution of a binder and granulation is carried out with stirring and heating, and the resulting granules are the dried and packed in single doses.

3. The process as claimed in claim 1, wherein after wetting said calcium compound with said binder solution at least one compound selected from the group consisting of pharmaceutically acceptable fillers and additives is added.

4. The process as claimed in claim 2, wherein after wetting said calcium compound with said binder solution at least one compound selected from the group consisting of pharmaceutically acceptable fillers and additives is added.

5. The process as claimed in claim 1 or 2, wherein the isoflavone content is 10 to 50 mg per dose.

6. The process as claimed in claim 1 or 2, wherein the calcium compound is present in inorganic form as carbonate, chloride, phosphate, or hydrogen phosphate or in organic form as glycerophosphate, levulinate, malate or citrate and the calcium ion content is preferably 400 to 1000 mg per dose.

7. The process as claimed in claim 1 or 2, in which the granules furthermore contain, per dose, 100 to 1000 IU of vitamin D3 or 50 to 100 mg of sodium monofluorophosphate.

8. The process as claimed in claim 1 or 2, wherein the soybean material is pulverulent and particles of the soybean material are present as an intimate mixture with particles of the calcium compound in granules which preferably contain a binder and optionally also a surfactant.

9. The process as claimed in claim 1 or 2, wherein the binder is soluble in an organic or water-containing organic solvent.

10. The process as claimed in claim 1 or 2, wherein the calcium compound is present in inorganic form and in addition up to 40% by weight of at least one filler is present.

11. The process as claimed in claim 1 or 2, wherein a at least one substance from the group consisting of the amino acids, vitamins, minerals and trace elements is added.

12. The process as claimed in claim 1 or 2, wherein the binder solution contains a surfactant.

13. The process as claimed in claim 1 or 2, wherein the dried granules are sieved to the desired particle size.

14. The process as claimed in claim 1 or 2, wherein each single dose comprises 200 to 800 IU of vitamin D3.

15. The process as claimed in claim 1 or 2, wherein said binder is selected from the group consisting of polyvinylpyrrolidone, polyethylene glycol 6000, and glucose syrup.

16. The process as claimed in claim 3 or 4, wherein said at least one compound is present in an amount of 5% to 35% by weight.

17. The process as claimed in claim 3 or 4, wherein said at least one compound is selected from the group consisting of maltodextrin, sugar alcohols, mono-saccharides, di-saccharides, vitamins, trace elements, and amino acids.

* * * * *